United States Patent [19]

Broadwin et al.

[11] Patent Number: 4,827,911
[45] Date of Patent: May 9, 1989

[54] METHOD AND APPARATUS FOR ULTRASONIC SURGICAL FRAGMENTATION AND REMOVAL OF TISSUE

[75] Inventors: Alan Broadwin, Brooklyn, N.Y.; Alexander Kreizman, Stamford, Conn.; Chana Puiam, Queens, N.Y.; Vaclav O. Podany, East New Fairfield; Leonard M. Emery, West Haven, both of Conn.

[73] Assignee: Cooper LaserSonics, Inc., Santa Clara, Calif.

[21] Appl. No.: 847,301

[22] Filed: Apr. 2, 1986

[51] Int. Cl.$^4$ .............................................. A61H 1/00
[52] U.S. Cl. .................................. 128/24 A; 310/317
[58] Field of Search ...................... 128/24 A, 305, 328, 128/303.13–303.15; 604/22; 310/317

[56] References Cited

U.S. PATENT DOCUMENTS

| | | | |
|---|---|---|---|
| 3,589,363 | 6/1971 | Banko | 128/24 A |
| 3,673,475 | 6/1972 | Britton, Jr. | 128/24 A |
| 3,693,613 | 9/1972 | Kelman | 128/24 A |
| 3,812,858 | 5/1974 | Oringer | 128/422 |
| 3,941,122 | 3/1976 | Jones | 128/24 A |
| 3,980,906 | 9/1976 | Kuris et al. | 128/24 A X |
| 4,063,557 | 12/1977 | Wachinichi et al. | 128/276 |
| 4,343,111 | 8/1982 | Inoue | 51/59 |
| 4,368,410 | 1/1983 | Hance et al. | 128/24 A X |
| 4,614,178 | 9/1986 | Harlt et al. | 128/24 A |
| 4,646,756 | 3/1987 | Watmough et al. | 128/24 A X |

FOREIGN PATENT DOCUMENTS 562279  4/1975  U.S.S.R. .......................... 128/24 A

Primary Examiner—Francis Jaworski
Attorney, Agent, or Firm—Vorys, Sater, Seymour and Pease

[57] ABSTRACT

A method and apparatus for periodically interrupting ultrasonic power applied to a ultrasonically vibrating tip to control its amplitude between high and low or zero amplitudes with a selectible duty cycle and repetition rate provides enhanced fragmentation and improves surgical control. The duty cycle may also vary as a function of a remotely sensed parameter such as tissue temperature.

64 Claims, 6 Drawing Sheets

METHOD AND APPARATUS FOR ULTRASONIC SURGICAL FRAGMENTATION AND REMOVAL OF TISSUE

BACKGROUND OF THE INVENTION

This invention relates to ultrasonic apparatus, and especially to ultrasonic surgical apparatus and methods for ultrasonic surgical fragmentation and removal of tissue. More particularly, this invention relates to a method and apparatus for pulsing or modulating the vibration of an ultrasonically vibrating tip to control its duty cycle for improving its cutting characteristics. Still more particularly, this invention relates to a method and apparatus for continuously controlling the duty cycle of an ultrasonic device, in discrete preset increments, between predetermined high and low amplitudes in variable programmed groups, or continuously in response to a remotely sensed parameter for accurately controlling ultrasonic energy delivered to the operating fluid.

Devices which effectively utilize ultrasonic energy for a variety of applications are well-known in a number of diverse arts. The application of ultrasonically vibrating surgical devices used to fragment and remove unwanted tissue with significant precision and safety has thus led to the development of a number of valuable surgical procedures. Accordingly, the use of ultrasonic aspirators for the fragmentation and surgical removal of tissue from a body has become well-known. Initially, the technique of surgical aspiration was applied for the fragmentation and removal of cataract tissue as shown, for example, in U.S. Pat. Nos. 3,589,363 and 3,693,613. Later, such techniques were applied with significant success to neurosurgery and other surgical specialties where the application of ultrasonic technology through a small, hand-held device for selectively removing tissue on a layer-by-layer basis with precise control has proven feasible.

Certain devices known in the art characteristically produce continuous vibrations having a substantially constant amplitude at a frequency of about 20 to 30 kHz up to about 40 to 50 kHz. U.S. Pat. No. 3,589,363 describes one such device which is especially adapted for use in the removal of cataracts, while U.S. Pat. No. 4,063,557 describes a device suitable for the removal of soft tissue which is particularly adapted for removing highly compliant elastic tissue mixed with blood. Such devices are continuously operative when a surgeon wishes to fragment and remove tissue, and generally operate under the control of a foot switch.

Certain limitations have emerged in attempts to use such devices in a broad spectrum of surgical procedures. For example, the action of continuously vibrating device did not have a desired effect in breaking up certain types of body tissue, bone, or concretations. Because the range of ultrasonic frequency is limited by the physical characteristics of a hand-held device, only the motion available at the tip was a focal point for improving the cutting characteristics of the instrument. This limited focus proved to be ineffective for certain applications because either the motion available at the tip was insufficient to fragment and remove hard tissue at a surgically-acceptable rate, or the available stroke and stroke amplitude was so large as to cause excessive damage to surrounding tissue and the vaporization of fluids at the surgical site so as to obscure the view of the surgeon. Accordingly, there has been a need in the art for a method and ultrasonic apparatus in which the cutting range and efficiency of the vibrating device can be extended for safe and efficacious tissue removal.

Thus, it is another overall objective to provide a method and ultrasonic apparatus for accurately controlling energy as it is transmitted to tissue so as to enhance its cutting action in both hard nd soft tissue, while maintaining the temperature in the surrounding tissue below a preset level. In this context it is desirable to utilize a higher stroke level than can otherwise be surgically tolerated without exceeding the allowable average energy, i.e., to simulate the effect of a high stroke level with a lower stroke level. It is also an objective to improve the visibility and control of the cutting action when fragmenting soft tissue and to utilize higher stroke levels for improved but safe fragmentation without damage to surrounding tissue areas as is characteristic of prior art devices.

In addition, since it is known that precisely controlled heating of certain types of cancerous and tumorous tissue may have a beneficial effect, it is another overall objective of this invention to provide a method and apparatus for precisely raising the temperature in tissues surrounding the tumorous growth to a preset level.

It is apparent that prior art concepts did not suggest such an invention. For example, U.S. Pat. No. 3,812,858 describes a dental electrosurgical device known to the art which regulates the application of RF power through an active electrode to a patient according to the resistance of the tissue, and further incorporates a duty cycle timer to regulate the period of active current flow and interrupt repeatedly active current flow to the patient. However, such relatively lengthy periods of interruption are not practicable in an ultrasonic unit which can cause the surgeon to have to wait for a reapplication of power, perhaps at crucial points in the surgery, and such techniques have not been applied to ultrasonic surgical apparatus of the type with which this invention is concerned.

In an ultrasonic machining method and apparatus, as discussed in U.S. Pat. No. 4,343,111, the vibratory oscillations applied to the machining tool are periodically interrupted so that the oscillations are applied in the form of a series of time-spaced bursts, for ultrasonically machining irregular contours. Such a device does not suggest its applicability to ultrasonic surgery or instrumentation and the technique there discussed is hardly directed to the problem solved by this invention.

The objects described above and other purposes of this invention will become apparent from a review of the written description of the invention which follows, taken in conjunction with the accompanying drawings.

SUMMARY OF THE INVENTION

Directed to achieving the foregoing objects of the invention and to providing a solution to the problems there noted, the apparatus according to this invention includes an improvement in a surgical device of the type which comprises an ultrasonically actuated handpiece, an ultrasonic generator, a control system, a control panel cooperating with the control system, and a footswitch for controlling the on/off state of the power as delivered to the handpiece. The improvement comprises a means for periodically pulsing the ultrasonic vibrating tip at a relatively high rate of speed at a repetition rate determined by the system response and the optimum fragmentation rate. In a preferred embodiment, the on/off state of the power continuously supplied to the ultrasonically-vibrating tip is pulsed between an "on" and "off" state at a frequency of about 33 Hz at a duty cycle within a range of about 1 to 2 (50%) to about 1 to 6 (16.67%). In an alternative, the power supply is pulsed at a rate which causes the amplitude of the ultrasonically-vibrating tip to vary between a high amplitude and a relatively low amplitude according to the pulse frequency. Thus, the waveform provided to the ultrasonic tip is, in effect, an ultrasonic carrier wave of about 23 kHz modulated by the periodically-applied pulse modulating wave. Circuit means are representatively illustrated for achieving this result in cooperation with a system known to the art.

In accordance with another aspect of the invention, a method is provided for pulsing an ultrasonically-vibrating tip on and off at a relatively high rate of speed to achieve an improved and faster cutting action on bone, cartilage and other hard tissue. Such a method eliminates or reduces the burning or adverse heating of surrounding bone and cartilage, while apparently reducing the force necessary to advance the tip through such hard tissue. It also precludes vaporization of the irrigation fluid, tissue, and other fluids which might otherwise obscure the vision of the attending surgeon. The method is characterized (a) in the step of controlling the duty cycle, i.e., the time on versus the time off or at a lesser stroke, so that the instrument can achieve a higher stroke level for improved but safe fragmentation without corresponding tissue damage to surrounding areas, and (b) setting the duty cycle so as to impart a predetermined level of energy or heat to the tissues surrounding a morbid or malignant growth to reduce or destroy the unwanted cells therein. According to the method of the invention, the duty cycle of the device is controlled continuously, in discrete preset increments, in variable preprogrammed groups, or continuously based upon a remote sensed parameter, such as temperature, in the operative field to yield a closed loop system. Circuit means are disclosed for achieving the method according to the invention.

BRIEF DESCRIPTION OF THE DRAWING

Other features, aspects, and characteristics of the invention will be apparent from the following descriptions.

In the drawings.

DETAILED DESCRIPTION OF PREFERRED EMBODIMENTS

Figure 1:
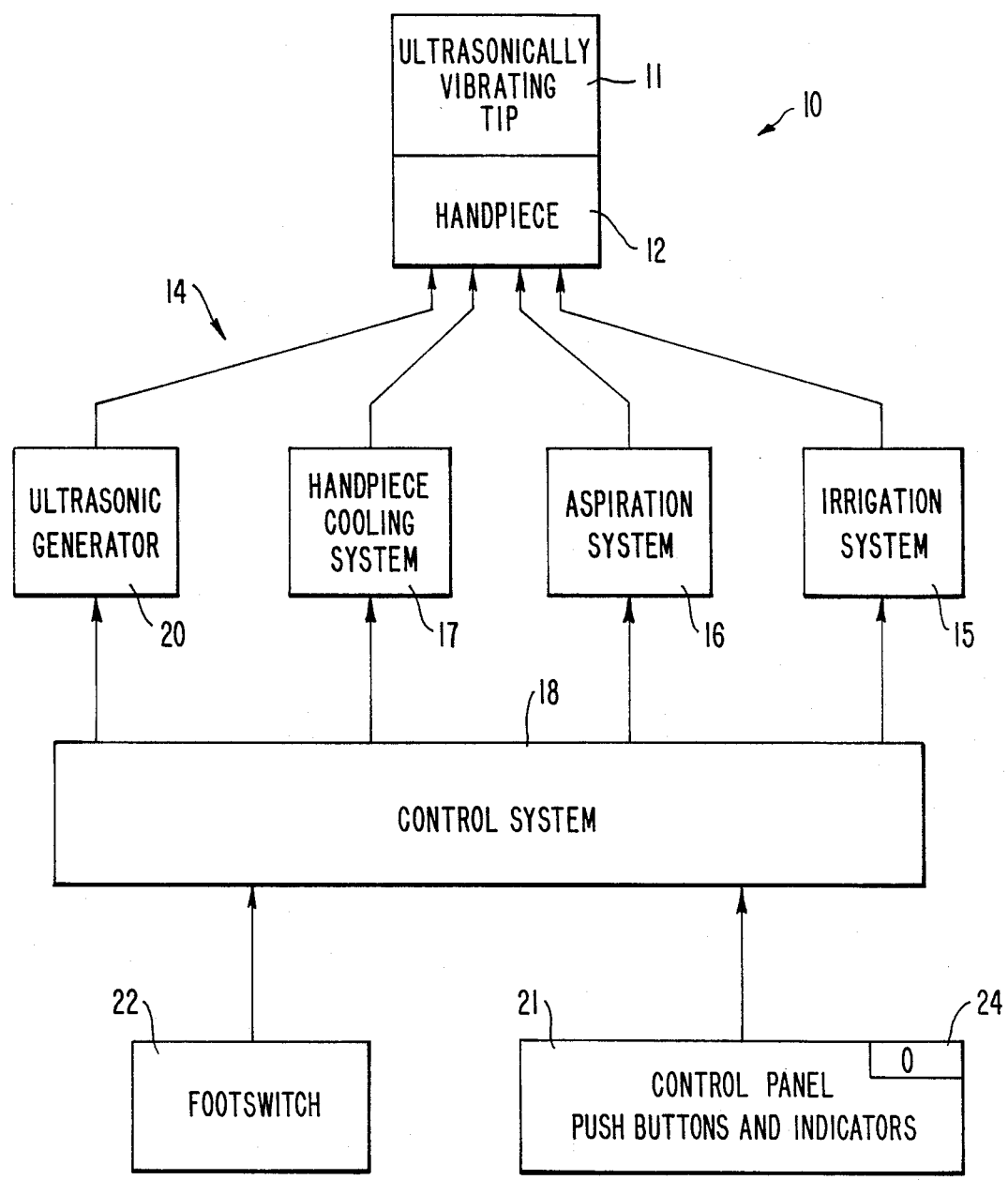
FIG. 1 is a functional block diagram of an ultrasonic surgical system known in the art.

In order to better understand the method and apparatus according to the invention relative to a conventional prior art system, such a conventional system, commercially available from the assignee of this application, will be discussed in connection with FIG. 1. The block diagram of FIG. 1 is representative of a commercially available device currently on the market under the mark CUSA NS-100. The system, designated generally by the reference numeral 10, incorporates several major functional systems available at a handpiece 12 for effectively removing tissue from a body. Those systems include a vibration system, designated generally by the reference numeral 14; an irrigation system 15; a suction system 16; and a handpiece cooling system 17; which cooperate with a control system 18 as is thus well-known. An ultrasonically-vibrating surgical tip 11 forms part of the handpiece 12 and is caused to vibrate longitudinally thereby fragmenting tissue in contact with its end. In such an embodiment, the level of vibration is manually and continuously adjustable to vary the amplitude of the tip. The irrigation system is controlling a flow of sterile irrigating solution from an IV source to a coagulant space between an outer surface of the surgical tip 11 and an inner surface to cause the fluid to exit near the tip 11 where it enters the operating field and suspends fragmented particles. The aspiration system 16 includes a pump for applying suction to the hollow surgical tip 11 to aspirate fluid through an end of the tip 11 for deposit in a disposable container.

An ultrasonic generator 20 provides electrical energy at ultrasonic frequencies to the handpiece 12, and in particular to drive coils within the handpiece 12 to control the vibrational stroke of the tip 11. Each of the foregoing systems and the ultrasonic generator is controlled by a control and interlock system 18 in cooperation with a control panel 21. In operation, after the system 10 is itself turned on with an appropriate push button at the control panel 21, the vibration of the handpiece 12 and delivery of ultrasonic energy from the ultrasonic generator 20 to the handpiece 12 is under the control of a footswitch operated by the surgeon. In this system, while the foot switch 22 is depressed and the system 10 is on, ultrasonic energy from the generator 20 is continuously and uninterruptedly provided to the tip 11 or the handpiece 12.

The ultrasonic generator 20 provides power to drive the tip 11 of the handpiece 12, preferably at a frequency of 23 kHz, and, by way of a signal derived from a handpiece feedback coil, which monitors and controls the amplitude of the stroke of the tip. A prior art feedback control system is shown in U.S. Pat. No. 4,063,557 which may be utilized to achieve these functions, the disclosure of which is hereby incorporated by reference. In its physical embodiment, the control system 18 includes a control input cooperating with the footswitch 22 for adjusting the vibration in circuit with an input relay on a control circuit module. The footswitch is connected to the control input for controlling the continuous on/off state. While the control system 18 includes, in a practical embodiment, a number of other control subsystems, such are not relevant or modified by the application of the invention here disclosed.

Figure 3:
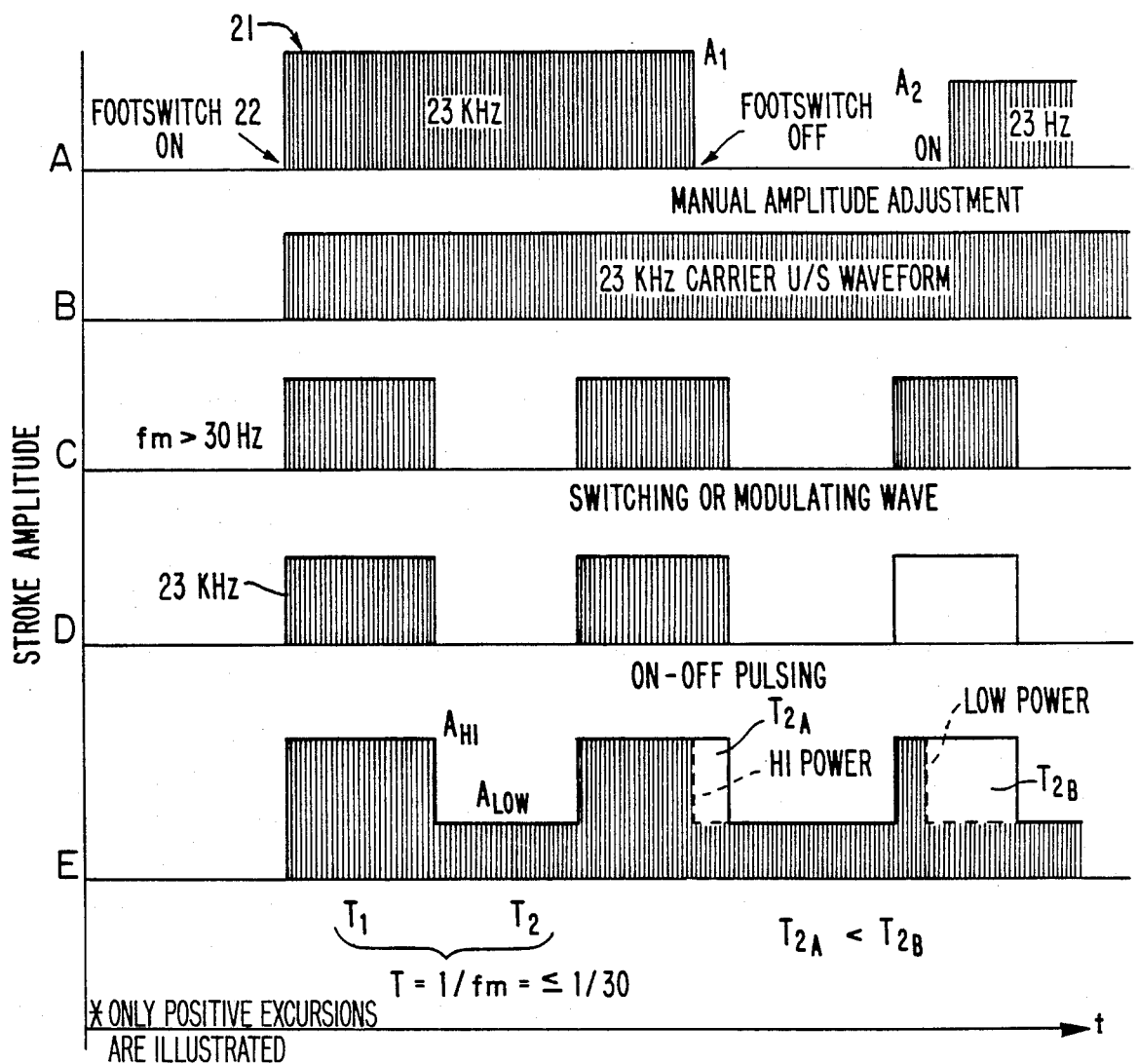
FIGS. 3A-3E are diagrams showing a continuous delivery of ultrasonic energy to an ultrasonically-vibrating handpiece in the prior art, and as modified under the invention illustrating manually-adjusted variations and modulated variations in stroke amplitude.

The control panel 21 includes a potentiometer 24 for adjusting the maximum stroke amplitude for the vibrating tip 11 on the handpiece, which is usually set by the surgeon. Thus, with the power to the system 10 on, and the footswitch 22 depressed, ultrasonic power is continuously, and selectively adjustably, delivered from the ultrasonic generator 20 to the handpiece 12 and hence to the vibrating tip 11. FIG. 3A shows the continuous application of such energy in the curve 21 at a typical frequency of 23 kHz. As illustrated by the curve 21, the amplitude of the stroke may be adjusted (by adjustment of the potentiometer 24) while the footswitch is off, thereby to establish a differing stroke amplitude for the tip.

Figure 2:
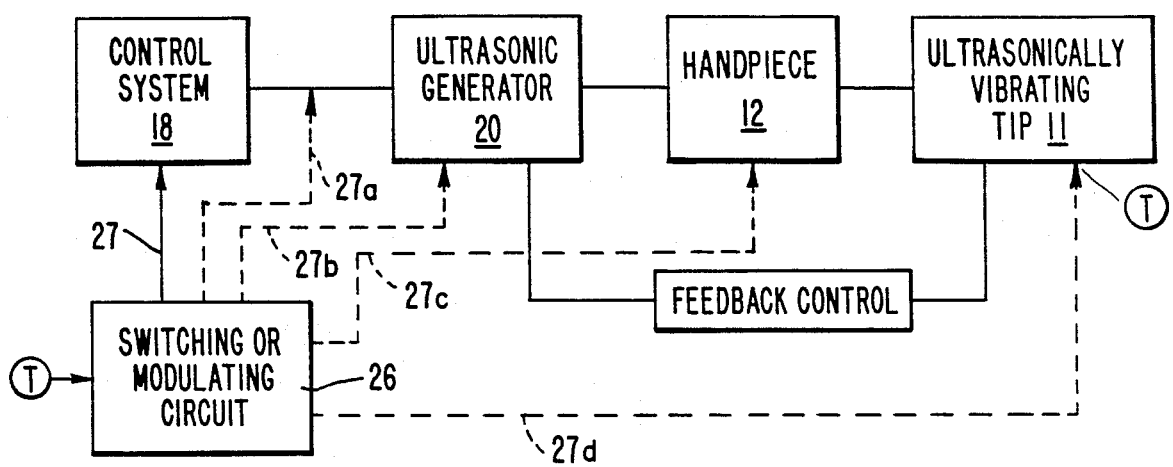
FIG. 2 is a functional block diagram of a portion of FIG. 1 to which the invention is applicable.

FIG. 2 illustrates the basic concept of the invention in a simplified block diagram of a portion of the block diagram of FIG. 1. A switching circuit 26 is connected to the control system 18 and cooperates therewith for periodically interrupting the ultrasonic vibrations from the ultrasonic generator 20 to the vibrating tip 11. The connection between the switching control circuit 26 and the control system 18 is depicted by the solid line 27. However, the circuit 26 could alternatively be connected to or cooperate with other systems, as shown by the dotted lines 27a, 27b, 27c, and 27d. In effect, the ultrasonic carrier waveform normally applied to the handpiece 11 (FIG. 3A) while the footswitch 22 is depressed is modulated by a modulating waveform, as shown in FIGS. 3B and 3C, to rapidly interrupt the ultrasonic power seen by the tip 11 for reasons to be discussed, thus to produce the applied waveform shown for a generalized case in FIG. 3E.

The apparatus shown in FIG. 2 is arranged and constructed so that the switching or modulating control circuit 26 causes the ultrasonic power for the ultrasonic generator to be delivered to the tip 11 of the handpiece 12 in a precisely controlled fashion. In one aspect of the invention, the ultrasonic power, preferably delivered at 23 kHz, is periodically interrupted by the modulating output from the switching control circuit 26 to vary the amplitude of the delivered waveform to the handpiece 12 continuously between a high amplitude, governed by the amplitude of the control setting on the potentiometer 24 on the control panel, and a low amplitude determined electronically at a suitable low level. Another aspect of the invention according to the method is to vary the amplitude between a predetermined high amplitude and an off state on a modulated periodic basis, as shown in FIG. 3D. The repetition rate is determined to be sufficiently rapid so that while the footswitch is depressed, the surgeon does not distractedly sense that he is waiting for the machine to operate while the periodic interruption of the delivered ultrasonic signal is providing a beneficial effect to his cutting. Thus, the repetition rate must be sufficiently high that the surgeon is not aware that the handpiece has shut off. Thus, for example, a suitable repetition rate is believed to be at least 30 Hz or higher, and the exact frequency is determined by the system response and the optimum fragmentation rate for particular hard tissue.

The repetition rate of the modulating frequency establishes the waveform of the delivered modulated ultrasonic carrier wave form as is shown in FIG. 3E. Thus, FIG. 3E shows a modulated 23-kHz carrier wave, shown unmodulated in FIG. 3B and delivered while the footswitch 22 is depressed representing ultrasonic energy as normally applied in the embodiment in FIG. 1, modulated according to the high/low (or on-/off) modulating influence established by the switching control circuit 26.

The waveform of FIG. 3E is presently preferred rather than an on/off wave form, such as shown in FIG. 3D, because one of the problems of an electro-acoustic system is that it is difficult and relatively slow in a mechanical sense to start and to shut off. That relative slowness is not determined by the electronic portion of the system limiting the startup or repetition rate, but rather by the mechanical parts in the vibrator itself. It has been learned that it takes significant amounts of times, measured in tens of milliseconds, to initiate vibration of the vibrating tip on the handpiece 12. During this startup or transient period, the conditions for the driving circuit for the tip 11 are relatively adverse in that the load is very low and is changing from inductive to capacitive. These adverse conditions must therefore be accommodated in the physical characteristics of the vibrator on the handpiece 12 and by the tip 11 to handle additional stresses. In addition, when the vibrating tip 11 is subjected to such significant additional stresses, a shorter and possibly a significant shorter life will result.

Thus, in order to shorten the start up time and reduce the related stresses on both the electronic and mechanical components, it is advantageous not to turn off the vibrations completely, as in one embodiment of this invention as shown in FIG. 3D, but rather to switch between two amplitudes, i.e., a working amplitude $A_{hi}$ selected by the surgeon by manipulation of the potientiometer 24 on the control panel 21, and a standby amplitude $A_{low}$ which will be a low amplitude as shown in FIG. 3E. The low amplitude can either be preset electronically, as in another embodiment of this invention, or may be as low as practical so that its only function is to keep the system vibrating. On the other hand, the low amplitude can also be made adjustable by the surgeon.

The modulating frequency of FIG. 3C determines the periodicity of the modulating wave and the relative periods between the application of the high amplitude and the application of the low amplitude determines the duty cycle. Thus, referring to FIG. 3E, for a period T, the duty cycle is determined by the ratio of $T1/T1+T2$, where the period T is determined by the sum of $T1+T2$; T1 is the period in which the amplitude is high, and T2 is the period in which the amplitude is low. Stated another way, the duty cycle is the ratio of the period of application of high power to the total period of application of power in each cycle. Thus, it is another aspect of the method and apparatus of this invention to control the duty cycle for the applied ultrasonic energy from the ultrasonic generator 20 to the handpiece 12.

Such a method and apparatus according to the invention control the fragmentation rate of the ultrasonic surgical system 10 wherein a surgeon may select the duty cycle or, the duty cycle may be set electronically or even automatically in response to a derived control signal to vary the duty cycle. Moreover, the use of a variable duty cycle by varying the relative amplitudes and periods of the application of the high and low strokes of the vibrating tips 11 acts to control the temperature of the tissues surrounding the operating areas. Such control of the duty cycle will thus permit hard tissue to be fragmented by increasing the stroke to a high amplitude for some limited period within the period of the modulating wave while permitting the heat transferred to the tissue to be controlled. It is known that when tissue is being fragmented, ultrasonic energy is transferred from the tip of the handpiece to the tissue. Some portion of the energy transferred is used to fragment the tissue, while a subportion is absorbed by the tissue and results in heating it. In an extreme case, tissue may be burned or vaporized creating an undesirable effect. Thus, a control of the type utilized in this invention prevents overheating of healthy tissues to the point of destruction.

On the other hand, such control is of value in therapeutically treating tumor cells. It is known that certain fast growing tumor cells are sensitive to elevated temperatures and are damaged by such higher temperatures. In accordance with another aspect of the invention, by sensing the temperature of the healthy tissue adjacent to the tumorous tissue being removed, such temperature as sensed can be utilized to vary automatically the duty cycle of high and low strokes to individually elevate the temperature of the tumor signals to a maximum without destroying the adjacent healthy tissues. In accordance with the method for this application, the low amplitude should be set as low as possible, for example 1 mil or less, and the duty cycle may be variable from about 10% to about 95% to nearly 100% as a function of temperature.

A convenient way for providing functional circuitry to perform the method according to the invention is to utilize a standard PWM controller as used in switching power supplies modified in one aspect of the invention to utilize a signal for controlling the switch as a function of temperature and noting that the switching frequency is low, such as in the 30 to 100 Hz range.

FIG. 2 thus shows a functional block diagram for modifying the conventional control system 18 of the surgical aspirator 10 as shown in FIG. 1. In the main, the existing equipment is modified to add a low amplitude adjustment potentiometer and utilizing the high amplitude adjustment potentiometer in the switching circuit in combination with a controlled switch to achieve the desired results of the invention.

Figure 4:
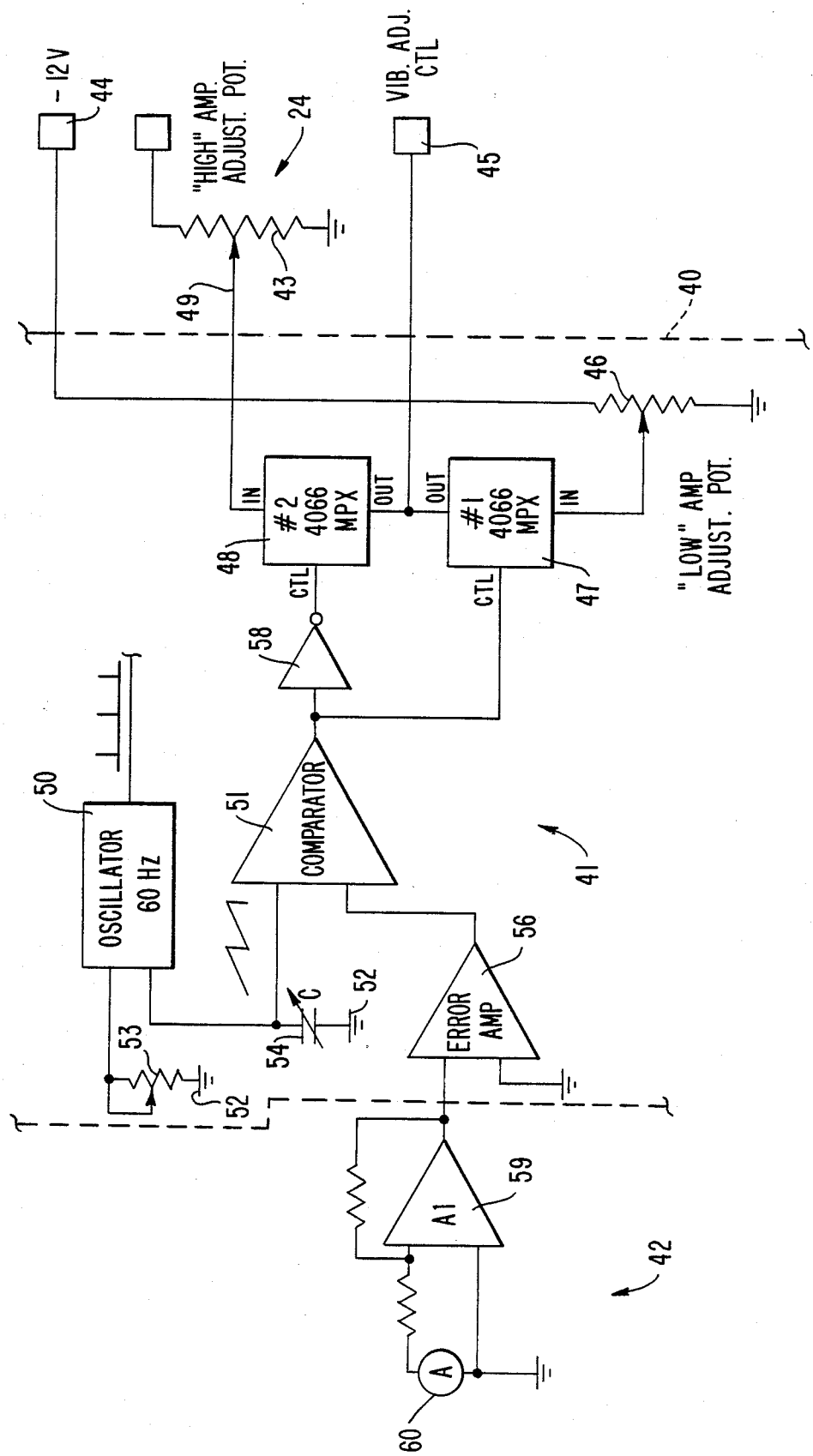
FIG. 4 is a block diagram of the fragmentation rate control circuit for controlling the apparatus of FIG. 1 and further including a temperature responsive input.

Thus, as more specifically shown in FIG. 4, the switching circuit for the CUSA 100 as shown to the right of the broken line 40 is modified by the inclusion of a duty cycle modulator designated generally by the reference numeral 41. The duty cycle modulator 41 is responsive, in one embodiment, to a thermal probe or other remote sensor of a selected parameter designated generally by the reference number 42. The high amplitude adjustment potentiometer 24 on the control panel is shown as comprising a potentiometer 43, a bias source as shown at 44 and a vibration adjustment control at 45 as are known in the existing system. The bias source 44 is also connected to a low amplitude adjustment potentiometer 46 which provides an input for a low amplitude control switch 47. A high amplitude control switch 48 has its input control connected to a wiper 49 on the high amplitude adjustment potentiometer 43.

An oscillator 50 is set to operate at the desired frequency, such as 30 Hz or more, and generates a ramp voltage for a comparator 51. The oscillator is connected to a source of reference potential, such as ground 52, through a resistor 53, while the input to the comparator 51 is connected to a source of reference potential 52 through a capacitor 54. A reference signal, or the output signal from the remote sensor 42, is applied through an error amplifier 56 to the other input of the comparator 51. The output of the comparator 51 controls the bilateral switch 47, while the complementary output of the comparator 51 through the an inverter 58 controls the output of the second bilateral switch 48.

The switches 47 and 48 thus form a multiplexer which alternately and for varying time durations switches the voltage from the surgeon-controlled high vibration adjustment potentiometer 24 and from the preset low amplitude potentiometer 46 to the vibration adjustment control on the system in FIG. 1. In the alternative, the low amplitude adjustment potentiometer could be a preset source of reference voltage to predetermine the low amplitude or, in a limiting case, could be ground, wherein the switch 47 could be eliminated, in order to switch the circuit between an on/off position subject to the limitations discussed above.

The remote sensor 42 comprises a thermal probe 60 for sensing the temperature at a predetermined site in the vicinity of the surgery, such as at adjacent tissue. In the alternative, other parameters, such as fragmentation rate, vapor generation, or the like, may be used as a control parameter for the input to the duty cycle modulator 41. The output of the probe 60 is amplified by an amplifier 59 prior to providing the input to the error amplifier 56.

In operation, when the sensed temperature input is low, the duty cycle is high, permitting a relatively longer period of high amplitude vibration, caused by a relatively longer "on" period for the switch 48. When the temperature is increasing, or higher than desired, the duty cycle modulator acts to increase the period of low amplitude stroke of the tip of the ultrasonic vibrator 11, thus reducing the energy applied to the overheating or overheated tissue.

Figure 5:
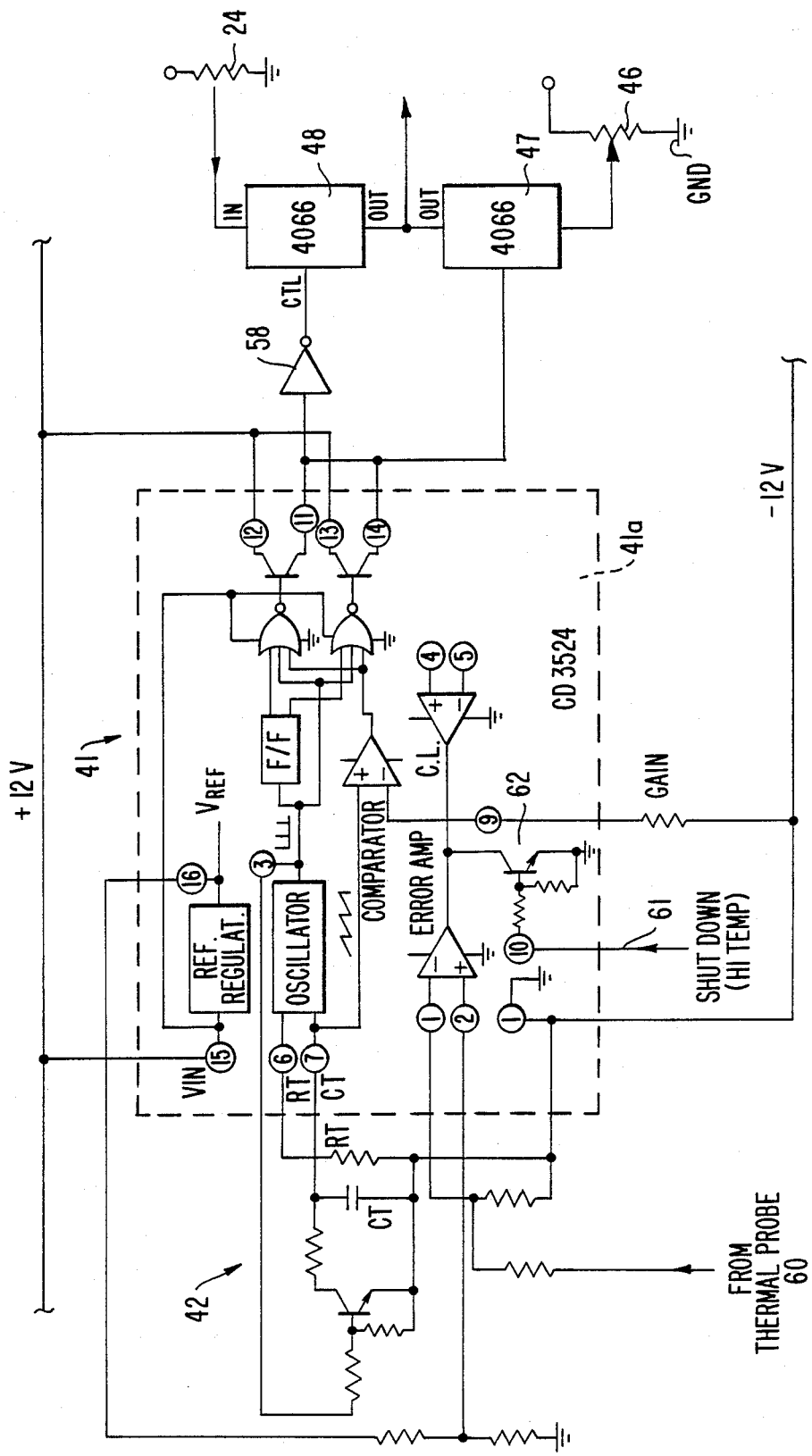
FIG. 5 is a circuit block diagram similar to FIG. 4 showing a system of temperature control by using pulse wave modification with a particular controller circuit.

FIG. 5 shows a block diagram in slightly greater detail for implementing the features of FIG. 4 using a CD3524 controller 41a to achieve the same results and functions. Thus, detailed discussion is not believed to be necessary.

The circuit of FIG. 5 further includes a modification for interrupting its operation in the event of excessively high temperature at the operating site. Thus, a signal is applied via a lead 61 to a shutdown signal amplifier 62, having an output connected to an input of the comparator on the PWM controller 41a.

Figure 6:
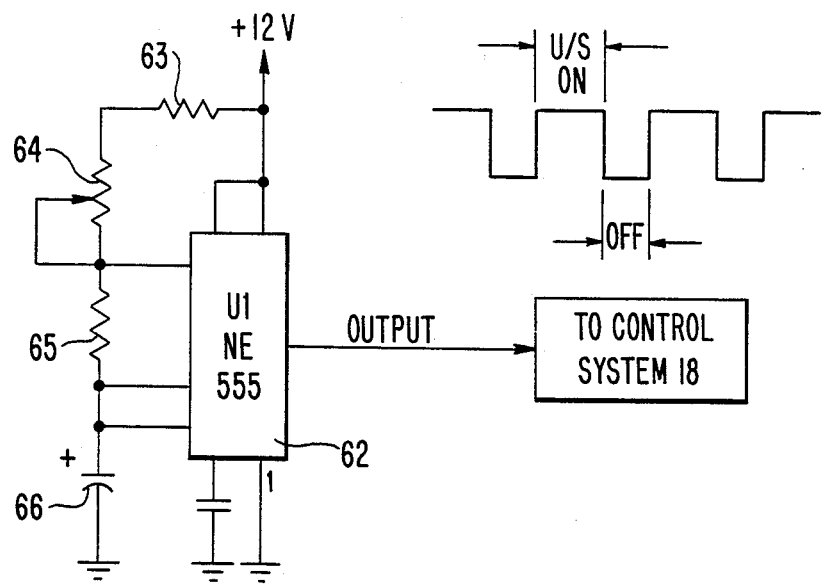
FIG. 6 is a block diagram of an input control circuit for an ultrasonic surgical aspirator in accordance with a preferred embodiment with variable pulse control for continuously adjusting on-time.

The circuit of FIG. 6 is a convenient one for providing a continuous "on" time adjustment to the input of the system of FIG. 1, and in particular to its input control relay. In FIG. 6, a trigger circuit 62 provides a timed output signal as shown in the figure. A resistor 63 in series with a variable resistor 64 determines the "on" time for the output of the trigger circuit, so that the minimum "on" time is established by the value of the resistor 63. The variable resistor 64 adjusts the "on" time in cooperation with the resistor 65 and the capacitor 66, whereas the "off" time is determined only by the resistor 65 and the capacitor 66, as is well known in the art. During the "on" time for the trigger circuit 62, the output signal is high to trigger the ultrasonic generator 20 through the control system 18 of FIG. 1.

Figure 7:
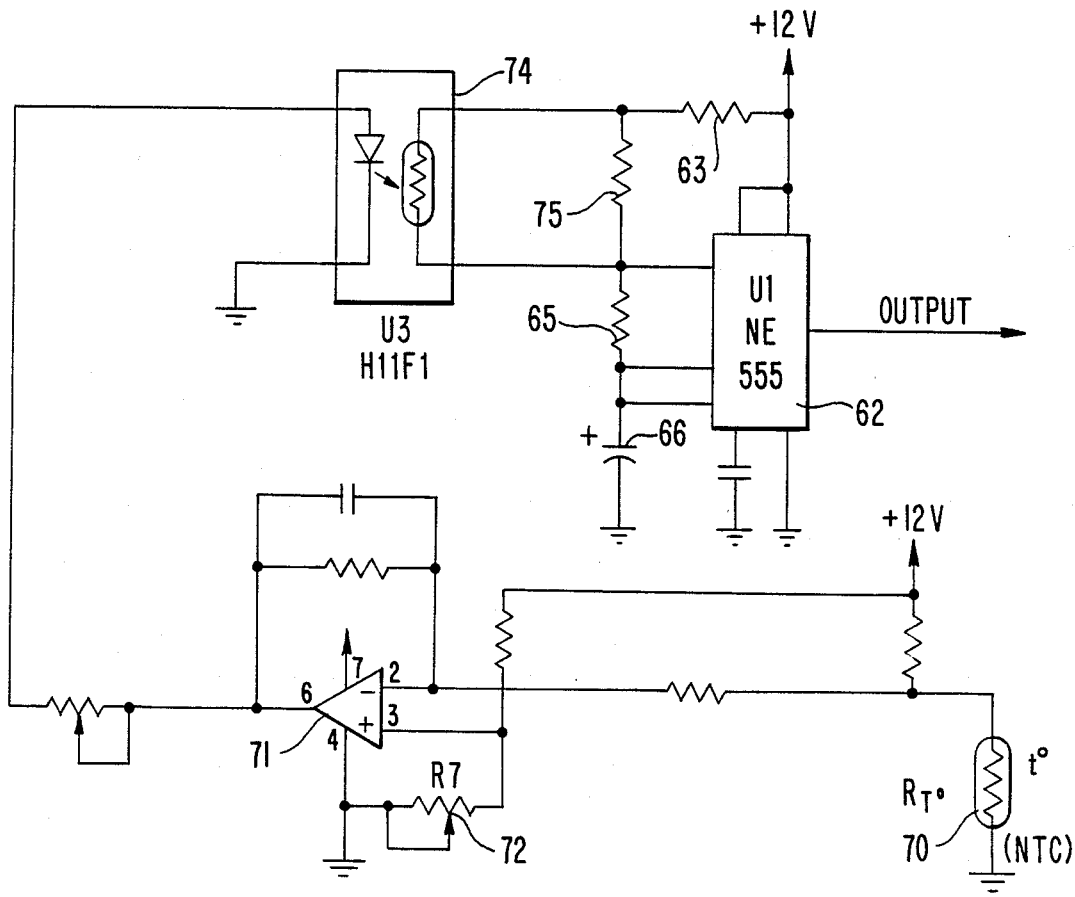
FIG. 7 is a schematic diagram of another input control circuit for an ultrasonic surgical aspirator in accordance with another embodiment of the invention to control temperature of the operating field.

FIG. 7 shows a suitable schematic, incorporating circuit elements like those shown in FIG. 6, for controlling the temperature of the operating field to less than a predetermined value by limiting the "on" time of the ultrasonic vibrations. The impedance of a negative temperature coefficient thermosensor 70 will change with the sensed temperature. The sensor 70 is located at the site where temperature is to be monitored. Since the thermosensor 70 is part of the feedback of a comparator 71, the desired temperature is set by the value of a potentiometer 72 connected between the output and input of the comparator 71, when the temperature rises, the output of the comparator 71 rises and the value of the impedance of the thermosensor 70 rises. This cumulative effect results in decreasing the "on" period because a second thermosensor 74 having its input in circuit with the output of the comparator 71 is in parallel with a resistor 75 in the feedback circuit of a logic switching circuit 62. Since the impedance of sensor 74 is in parallel with the resistor 75, the on period from the switching circuit 62 decreases, and in response to increasing sensed temperature. On the other hand when the temperature decreases, the "on" time increases. The output, as in FIG. 5, is connected to a relay in the control circuit of the existing system shown in FIG. 1.

As can thus be understood, during the "on" time, the output of the trigger circuit 62 is high so that the vibrating tip of the handpiece 10 is actuated. When the signal becomes low, ultrasonic power is momentarily deactuated before again being actuated when the signal again goes high. The trigger circuit shown in FIG. 8 operates the same way as the circuit shown in FIG. 5 except that the "on" time may be discretely varied by selectively connecting any one of the plurality of resistors 64A, 64B, 64C, or 64D, or some combination thereof, into the RC network of the trigger circuit 62. Thus, the off time is determined by the resistor 65 and capacitor 66 as it was in connection with the trigger circuit shown in FIG. 5.

Each of the resistors 64A, 64B, 64C, and 64D is respectively in a series circuit with an associated switch 64A', 64B', 64C', and 64D', respectively controlled by the logic control circuit, designated generally by the reference numeral 78.

Figure 8:
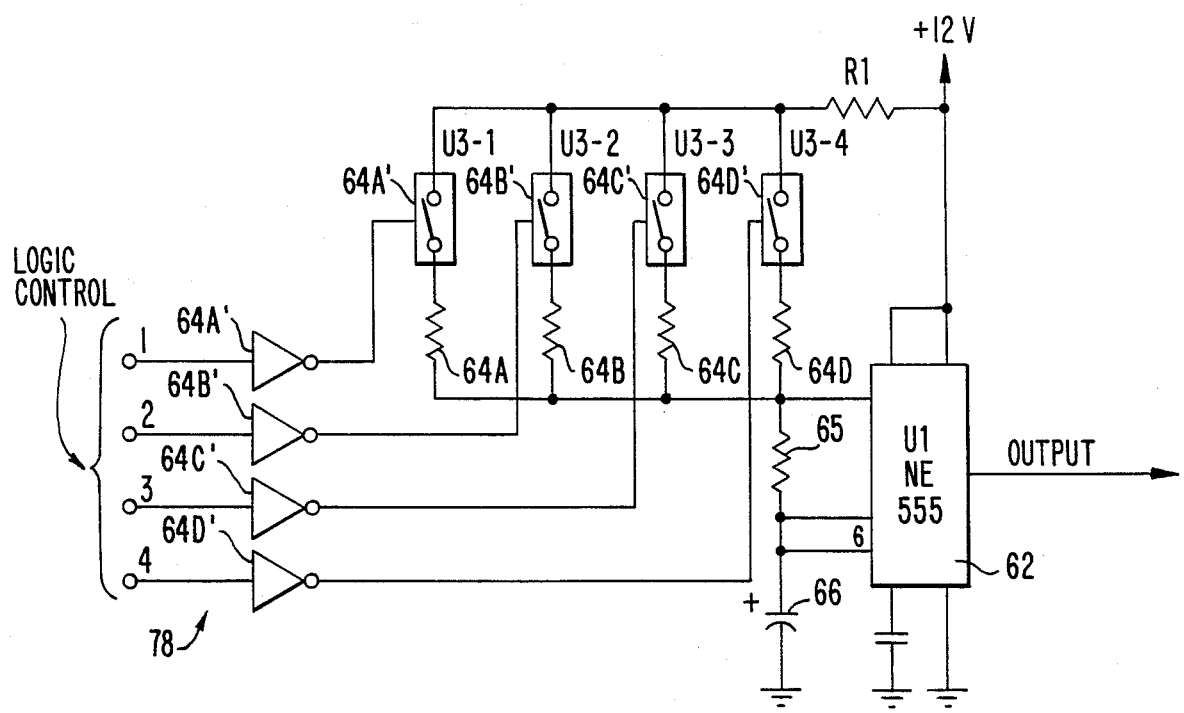
FIG. 8 is a typical input control circuit for producing a continuous, discrete on-time adjustment.
Figure 9:
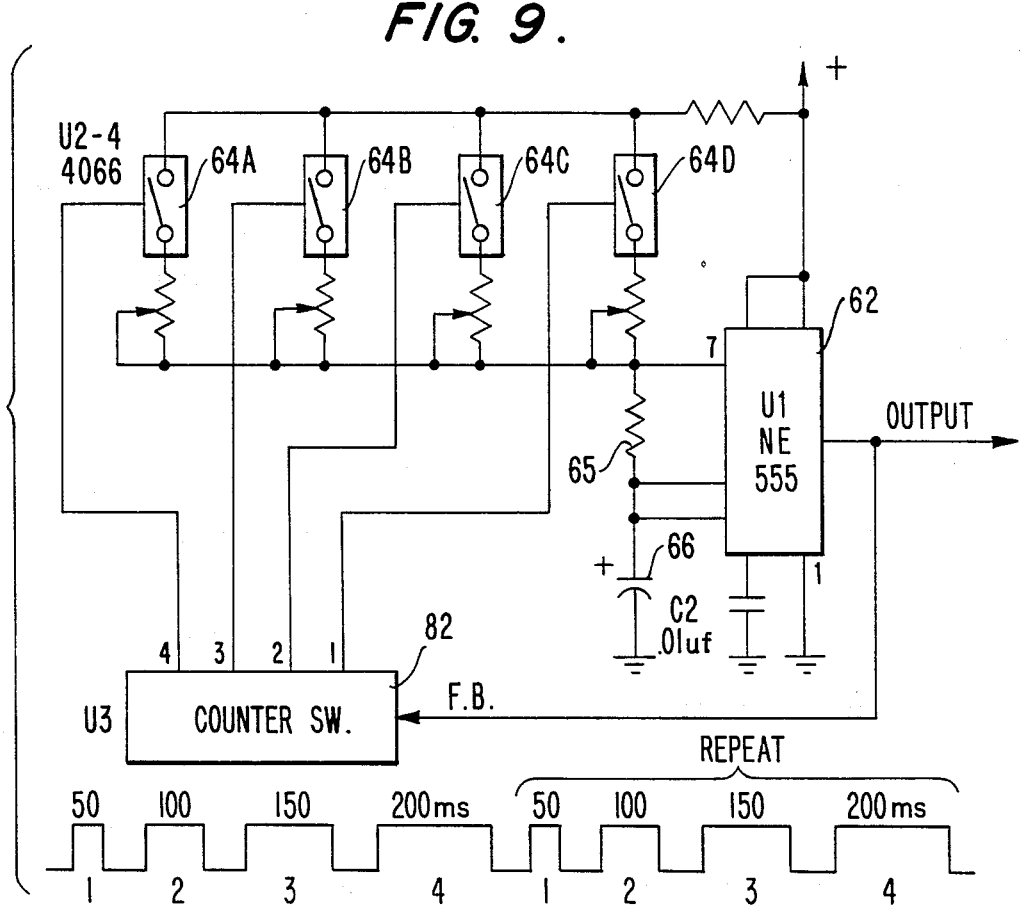
FIG. 9 shows an input control circuit for producing, bursting modulating pulses according to a predetermined sequence.

The trigger circuit 62 shown in FIG. 9 provides, similarly to FIG. 8, a fixed "off" time determined by the resistor 65 and capacitor 66, but the "on" time provided by the RC network varies sequentially. Resistors 64A-64D are sequentially connected into the RC network by a counter switch 82 which is actuated each time the output of the trigger circuit 62 becomes low. Thus, when resistors 64A 64D are set to respective suitable values, a first "on" time, a second on time, a third "on" time, and a fourth on time are predetermined values, such as 50, 100, 150, and 200 m sec., which can be produced in a repeated sequence, thereby providing a sequentially varied repetition rate.

The control circuit according to the invention may be used to provide a number of different modes of operation for the circuit of FIG. 1. For example, a first mode may be a continuously operating mode which operates the handpiece in a normal manner as described in connection with FIG. 1. A second mode is a rapid on-off interruption of ultrasonic power typically at a frequency rate of 33 Hz with an on-off duty cycle of 1 to 2. A third mode is a rapid medium speed mode and operates at a frequency of 18 Hz and an on-off duty cycle of 1 to 4, as representatively illustrated by the right hand portion of FIG. 3E. Mode 4 is a slow mode which operates at a frequency of 7 Hz and an on-off duty cycle of 1 to 4. Finally, mode 5 is a slow mode which operates at a frequency of 5 Hz with an on-off duty cycle of 1 to 6. In each of the modes, the vibration setting is adjusted by external vibration adjusting potentiometer 45 in FIG. 4, while the frequency and duty cycle are adjusted electronically. Preferably, the amplitude is set while the system 10 is in the continuous mode, and an automatic interruption mode selected from among exemplary modes 1 to 4. The selected mode is thereafter locked in when the footswitch 22 is depressed and cannot be changed until the footswitch 22 is released. Further modification of the prior art circuitry to implement the teachings of this invention is within the skill in this art.

The ultrasonic fragmentation produced according to method and by the described apparatus in accordance with the present invention provides enhanced cutting action is both hard and soft tissue, particularly in bone and cartilage where ultrasonic fragmentation at a constant stroke amplitude provided by a known aspirator apparatus had little effect. In addition, since the present invention permits an average stroke amplitude to be used that is smaller than the stroke needed by constant amplitude aspirators for effective fragmentation, heating of tissue adjacent to the fragmentation site can be reduced without sacrificing surgical effectiveness.

The increased fragmentation effectiveness provided by the present invention both increases the speed of operation and reduces the force needed to push through hard tissue such as bone, thereby reducing operator fatigue and improving the operator's control of the aspirators. The use of a variable stroke amplitude in an ultrasonic surgical aspirator in accordance with the present invention also provides improved visual control of incisions made in soft tissue by providing improved fragmentation, thereby enhancing debris removal by the aspirator.

The improved control provided by varying the duty cycle of the high amplitude stroke of the vibrator, when used in cooperation with means for sensing the temperature of tissue adjacent to or near the incision made by an ultrasonic surgical aspirator, is also well suited for use in providing hypothermic treatment to surrounding tissue while removing a cancerous or tumorous growth. The improved thermal control provided by apparatus in accordance with the present invention permits adjacent tissue to be raised to a precisely controlled temperature that would not destroy healthy tissue but, at the same time would reduce the viability of any fast growing tumor cells that may have invaded adjacent tissue.

The invention has been described with particular reference to its presently preferred embodiments, but numerous modifications and variations within the spirit and scope of the invention as described herein and is defined by the claims will be apparent to one skilled in the art. For example, a feedback signal indicating fragmentation rate could be used to control the amplitude or duty cycle of the high amplitude stroke.

What is claimed:
1. An ultrasonic surgical apparatus comprising:
a surgical handpiece,
an ultrasonic tissue fragmenting tool adapted for ultrasonically fragmenting tissue at a surgical site of a patient,
said tool being supported by said handpiece,
said tool having an ultrasonically-vibratable tool tip,
a supplying means for supplying ultrasonic vibrations to said tool tip,
a switching means for automatically and repeatedly switching the amplitude of the ultrasonic vibrations of said tool, during a tissue fragmenting procedure at the surgical site, back and forth between a working high amplitude and a standby low ampli- tude which is a lower amplitude than said high amplitude, an aspirating means connected to said handpiece for aspirating, from the surgical site, fluid and tissue fragmented by said ultrasonically-vibrating tool tip, and an irrigating means connected to said handpiece for supplying an irrigating solution to the area of the surgical site for suspending the tissue particles fragmented by said tool tip.

2. The apparatus of claim 1 wherein said switching means switches the delivered vibration amplitude between said high and low amplitudes at a switching repetition rate which is sufficiently rapid whereby the operator of the apparatus does not distractedly sense said low amplitude.

3. The apparatus of claim 2 wherein said repetition rate is at least 30 Hz.

4. The apparatus of claim 1 wherein said low amplitude allows the tissue at the surgical site to cool off during the tissue fragmenting procedure.

5. The apparatus of claim 1 wherein said ultrasonic vibrations comprise an ultrasonic carrier wave of about 23 KHz.

6. The apparatus of claim 5 wherein said switching means provides a periodically-applied pulse modulating wave which modulates said ultrasonic carrier wave.

7. The apparatus of claim 1 wherein said switching means includes a feed-back loop, said high amplitude remains at a constant level during the tissue fragmenting procedure, and said switching means limits the amount of energy allowed by said feed-back loop.

8. The apparatus of claim 1 wherein said switching means includes a feed back means for measuring temperatures at the surgical site or surrounding area to ensure that the energy transmitted by said tool to the patient does not exceed allowable limits.

9. The apparatus of claim 1 wherein said switching means interrupts said high amplitude so that the energy levels delivered do not harm to the patient.

10. The apparatus of claim 1 wherein said supplying means comprises an ultrasonic generator.

11. The apparatus of claim 1 further comprising a controlling means for controlling the operation of said supplying means.

12. The apparatus of claim 11 wherein said switching means is operatively connected to and cooperates with said controlling means.

13. The apparatus of claim 1 further comprising a manual switch means having "on" and "off" positions for operatively connecting said supplying means to said tool.

14. The apparatus of claim 13 wherein said switching means switches between said low and high amplitudes when said manual switch means is in said "on" position.

15. The apparatus of claim 14 wherein said low amplitude is a zero amplitude.

16. The apparatus of claim 1 wherein said tool has a distal tool tip, said tool is hollow and defines a fluid passageway which communicates with said distal tool tip, and said aspirating means includes an applying means for applying suction to said tool to aspirate material adjacent said tool tip through said fluid passageway and away from the surgical site.

17. The apparatus of claim 1 wherein said switching means causes a duty cycle which is between about 15% and less than 100%.

18. The apparatus of claim 1 wherein said supplying means comprises a closed loop generator feed-back system.

19. The apparatus of claim 18 wherein said supplying means includes a high amplitude adjust potentiometer means which provides a reference signal for said closed loop generator feed-back system for setting said high amplitude.

20. The apparatus of claim 19 wherein said supplying means further includes a low amplitude adjust potentiometer means which provides a reference signal for said closed loop generator feed-back system for setting said low amplitude.

21. The apparatus of claim 19 wherein said switching means includes a timer circuit which switches with a predetermined sequence between said high and low amplitudes.

22. The apparatus of claim 1 wherein said low amplitude is zero, whereby said ultrasonic vibrations at a predetermined frequency are provided between an "on" state and an "off" state.

23. The apparatus of claim I further comprising an adjusting means for adjusting said high amplitude.

24. The apparatus of claim 1 wherein said switching means includes a low amplitude adjusting means for adjusting said low amplitude.

25. The apparatus of claim 24 wherein said low amplitude adjusting means includes a potentiometer means for adjustably setting said low amplitude.

26. The apparatus of claim 24 wherein said low amplitude adjusting means includes a circuit means for adjustably setting said low amplitudes.

27. The apparatus of claim 1 wherein said switching means includes an oscillator means for providing a predetermined modulating frequency to said tool.

28. The apparatus of claim 27 wherein said oscillator means provides a modulating frequency at about 30 Hz or greater.

29. The apparatus of claim 1 wherein said tool is pulsed by said switching means between said high amplitude and said low amplitude at a frequency of about 5 Hz or more.

30. The apparatus of claim 1 wherein said switching means includes a duty cycle control means for providing a variable preselected duty cycle for said high and said low amplitude vibrations.

31. The apparatus of claim 1 wherein said switching means includes a duty cycle control means for providing a variable preselected duty cycle for said high and said low amplitude vibrations, said duty cycle control means being responsive to a remotely sensed parameter.

32. The apparatus of claim 31 wherein said remotely-sensed parameter is temperature.

33. The apparatus of claim 32 wherein said duty cycle is decreased in response to increasing temperature.

34. The apparatus of claim 32 wherein said duty cycle is decreased when said remotely-sensed temperature rises to a predetermined value.

35. The apparatus of claim 32 wherein said duty cycle is increased when said remotely-sensed temperature is below a predetermined value to increase the temperature at the surgical site.

36. The apparatus of claim 31 wherein said remotely-sensed parameter is the rate said tool is fragmenting tissue at the surgical site.

37. The apparatus of claim 31 wherein said remotely-sensed parameter is the vapor generation at the surgical site.

38. The apparatus of claim 1 wherein said tool provides surgical removal of at least a part of the tissue to which it is applied, and wherein said switching means causes a change of the stroke amplitude of said tool at a repetition rate and a duty cycle so that the fragmenting procedure is not interrupted while said tool is fragmenting and aspirating the tissue.

39. The apparatus of claim 1 further comprising a temperature sensing means for sensing the temperature of tissue adjacent to the tissue to which said tool is being applied while applied thereto, and said switching means is responsive to said temperature sensing means to vary the amplitude of the stroke of said tool with a duty cycle that is a function of the adjacent tissue temperature.

40. The apparatus for claim 39 wherein said duty cycle is an inverse cycle function of said temperature.

41. The apparatus of claim 1 wherein said switching means includes a varying means for sequentially varying the repetition rate with which said amplitude is automatically varied between said high amplitude and said low amplitude according to a predetermined sequence.

42. The apparatus of claim 1 wherein said switching means controls the total time cycle of the interruption of said ultrasonic vibrations by the application of vibrations of said low amplitudes to less than 1,000 ms.

43. The apparatus of claim 1 wherein said switching means includes a modulating means for modulating an ultrasonic carrier signal at a frequency on the order of 30 Hz or more.

44. The apparatus of claim 43 further comprising a sensing means for sensing a parameter, to produce a parameter-based control signal representative thereof, said switching means being responsive to said parameter-based control signal to vary the duty cycle of the modulated ultrasonic signal.

45. The apparatus of claim 44 wherein said duty cycle lies within a range of about 50% to about 100%.

46. The apparatus of claim 1 wherein said supplying means comprises a general loop feed-back control system including a generator, and said switching means switches the amplitude setting of said generator, when said supplying means is in an "on" cycle thereof, between said high and low amplitudes.

47. The apparatus of claim 46 wherein said low amplitude is a zero amplitude.

48. An ultrasonic surgical apparatus for removing tumorous tissue from a patient with minimal resulting damage to the healthy tissue adjacent to the tumorous tissue comprising:
an ultrasonic tissue fragmenting tool,
a pulsing means for pulsing said tool with ultrasonic vibrations during the ultrasonic tumorous tissue fragmenting procedures at a rapid pulse rate between a working high amplitude for a first period of time and a standby low amplitude which is lower than said high amplitude for a second period of time,
a cycle time defined by said first period of time plus said second period of time,
a duty cycle defined by said first period of time divided by said cycle time,
a sensing means for sensing the temperature of the adjacent healthy tissue while the tumorous tissue is being fragmented during a fragmenting procedure, and
an adjusting means for automatically varying, as a function of the temperature sensed by said sensing means, said duty cycle.

49. The apparatus of claim 48 wherein said low amplitude is one mil or less.

50. The apparatus of claim 48 wherein said duty cycle is variable by said adjusting means from about 10% to nearly 100%.

51. The apparatus of claim 48 wherein said duty cycle is an inverse cycle function of the temperature sensed by said sensing means.

52. A method for the controlled fragmenting of unwanted tissue at a surgical site with reduced resulting heat damage comprising:
during an ultrasonic tissue fragmenting procedure at the surgical site using a vibratable tool of an ultrasonic fragmenting device, automatically and periodically interrupting at a rapid rate the amplitude of the ultrasonic vibrations delivered to the tool between a working high amplitude and a standby low amplitude which is a lower amplitude than said high amplitude.

53. The method of claim 10 wherein said periodically interrupting is characterized in that the duty cycle thereof is between about 15% and less than 100%.

54. The method of claim 10 wherein said low amplitude is a zero amplitude.

55. The method of claim 10 further comprising sequentially varying the repetition rate with which the stroke amplitude of said tool is varied between said high and low amplitudes according to a predetermined sequence.

56. An ultrasonic surgical apparatus comprising:
an ultrasonic tissue fragmenting tool adapted for ultrasonically fragmenting tissue at a surgical site of patient,
a supplying means for supplying ultrasonic vibrations to said tool,
a switching means for switching the amplitude of the ultrasonic vibrations of said tool, during a tissue fragmenting procedure at the surgical site, back and forth between a working high amplitude and a standby low amplitude which is a lower amplitude than said high amplitude, and
said supplying means further includes a low amplitude adjust potentiometer means which provides a reference signal for said closed loop generator feed-back system for setting said low amplitude.

57. An ultrasonic surgical apparatus comprising:
an ultrasonic tissue fragmenting tool adapted for ultrasonically fragmenting tissue at a surgical site of patient,
a supplying means for supplying ultrasonic vibrations to said tool,
a switching means for switching the amplitude of the ultrasonic vibrations of said tool, during a tissue fragmenting procedure at the surgical site, back and forth between a working high amplitude and a standby low amplitude which is a lower amplitude than said high amplitude,
said switching means including a duty cycle control means for providing a variable preselected duty cycle for said high and said low amplitude vibrations,
said duty cycle control means being responsive to a remotely sensed parameter, and
said remotely-sensed parameter being temperature.

58. An ultrasonic surgical apparatus comprising:

an ultrasonic tissue fragmenting tool adapted for ultrasonically fragmenting tissue at a surgical site of a patient, a supplying means for supplying ultrasonic vibrations to said tool, a switching means for switching the amplitude of the ultrasonic vibrations of said tool, during a tissue fragmenting procedure at the surgical site, back and forth between a working high amplitude and a standby low amplitude which is a lower amplitude than said high amplitude, said switching means including a duty cycle control means for providing a variable preselected duty cycle for said high and said low amplitude vibrations, said duty cycle control means being responsive to a remotely-sensed parameter, and said remotely-sensed parameter being vapor generation at the surgical site.

59. An ultrasonic surgical apparatus comprising:

an ultrasonic tissue fragmenting tool adapted for ultrasonically fragmenting tissue at a surgical site of a patient, a supplying means for supplying ultrasonic vibrations to said tool, a switching means for switching the amplitude of the ultrasonic vibrations of said tool, during a tissue fragmenting procedure at the surgical site, back and forth between a working high amplitude and a standby low amplitude which is a lower amplitude than said high amplitude, a temperature sensing means for sensing the temperature of tissue adjacent to the tissue to which said tool is being applied while applied thereto, and said switching means being responsive to said temperature sensing means to vary the amplitude of the stroke of said tool with a duty cycle that is a function of the adjacent tissue temperature.

60. An ultrasonic surgical apparatus comprising:
an ultrasonic tissue fragmenting tool, a pulsing means for pulsing said tool with ultrasonic vibrations at a rapid pulse rate during an ultrasonic tissue fragmenting procedure between a working high amplitude for a first period of time and a standby low amplitude which is lower than said high amplitude for a second period of time, a cycle time defined by said first period of time plus said second period of time, duty cycle defined by said first period of time divided by said cycle time, a controlling means for controlling said duty cycle, said controlling means controlling said duty cycle continuously based upon a remotely-sensed parameter in the operative field of said tool to yield a closed loop system, and said remotely-sensed parameter comprising temperature of tissue of a patient.

61. The apparatus of claim 1 wherein said controlling means controls said duty cycle continuously during the fragmenting procedure of said tool.

62. The apparatus of claim 60 wherein said controlling means controls said duty cycle in discrete preset increments.

63. The apparatus of claim 60 wherein said controlling means controls said duty cycle in variable preprogrammed groups.

64. A method for the controlled fragmenting of unwanted tissue at a surgical site with reduced resulting heat damage comprising:

during an ultrasonic tissue fragmenting procedure at the surgical site using a vibratable tool of an ultrasonic fragmenting device, periodically interrupting at a rapid rate the amplitude of the ultrasonic vibrations delivered to the tool between a working high amplitude and a standby low amplitude which is a lower amplitude than said high amplitude, sensing a remote parameter, and varying the duty cycle of said interrupting step as a function of said remotely-sensed parameter, and said remotely-sensed parameter being temperature.

* * * * *